(12) United States Patent
Zhang

(10) Patent No.: US 9,701,733 B2
(45) Date of Patent: *Jul. 11, 2017

(54) MASPIN-BASED TREATMENT OF CANCER

(71) Applicant: Northwestern University, Evanston, IL (US)

(72) Inventor: Ming Zhang, Glencoe, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/445,772

(22) Filed: Jul. 29, 2014

(65) Prior Publication Data

US 2014/0342990 A1 Nov. 20, 2014

Related U.S. Application Data

(62) Division of application No. 13/478,904, filed on May 23, 2012, now Pat. No. 8,791,233.

(60) Provisional application No. 61/489,514, filed on May 24, 2011.

(51) Int. Cl.
C07K 14/81 (2006.01)
A61K 38/00 (2006.01)

(52) U.S. Cl.
CPC ........ *C07K 14/8121* (2013.01); *C07K 14/811* (2013.01); *A61K 38/00* (2013.01)

(58) Field of Classification Search
CPC .............................. A61K 38/00; C07K 14/811
See application file for complete search history.

(56) References Cited

U.S. PATENT DOCUMENTS

| 8,791,233 B2 | 7/2014 | Zhang |
| 2002/0086019 A1 | 7/2002 | Wolf et al. |
| 2009/0138977 A1 | 5/2009 | Domon et al. |
| 2009/0263363 A1 | 10/2009 | Zhang |

OTHER PUBLICATIONS

Abraham et al., "Maspin functions as tumor suppressor by increasing cell adhesion to extracellular matrix in prostate tumor cells," J Urol, 2003, 169:1157-1161.
Al-Ayyoubi et al., "Maspin binds to urokinase-type and tissue-type plasminogen activator through exosite-exosite interactions," J Biol Chem, 2007, 282:19502-19509.
Al-Ayyoubi et al., "Crystal structure of human maspin, a serpin with antitumor properties: reactive center loop of maspin is exposed but constrained," J Biol Chem, 2004, 279:55540-55544.
Andreasen et al., "The plasminogen activation system in tumor growth, invasion, and metastasis," Cell Mol Life Sci, 2000, 57:25-40.
Bass et al., "Maspin Inhibits Cell Migration in the Absence of Protease Inhibitory Activity," J Biol Chem, 2002, 277:46845-46848.
Bass et al., "Binding of extracellular maspin to beta1 integrins inhibits vascular smooth muscle cell migration," J Biol Chem, 2009, 284:27712-27720.
Blasi & Carmeliet, "uPAR: a versatile signalling orchestrator," Nat Rev Mol Cell Biol, 2002, 3:932-943.
Biliran & Sheng, "Pleiotrophic inhibition of pericellular urokinase-type plasminogen activator system by endogenous tumor suppressive maspin," Cancer Res, 2001, 61:8676-8682.
Carter et al., "Epiligrin, a new cell adhesion ligand for integrin alpha 3 beta 1 in epithelial basement membranes," Cell, 1991, 65:599-610.
Cella et al., "Maspin is physically associated with [beta]1 integrin regulating cell adhesion in mammary epithelial cells," FASEB J, 2006, 20:1510-1512.
Chapman et al., "Role of urokinase receptor and caveolin in regulation of integrin signaling," Thromb Haemost, 1999, 82:291-297.
Conlon, "Preparation of 125I-Labeled Peptides and Proteins with High Specific Activity using IODO-GEN", 2nd Edition Ed. (2002) The Protein Protocols Handbook (Walker, J. M.,Ed.), Humana Press Inc, Totowa, NJ.
Cortese et al., "Clathrin and LRP-1-independent constitutive endocytosis and recycling of uPAR," PLoS One, 2005, 3:e3730.
Czekay et al., "Direct binding of occupied urokinase receptor (uPAR) to LDL receptor-related protein is required for endocytosis of uPAR and regulation of cell surface urokinase activity," Mol Biol Cell, 2001, 12:1467-1479.
Dass et al., "Evolving role of uPA/uPAR system in human cancers," Cancer Treat Rev, 2008, 34:122-136.
Degryse et al., "Urokinase/urokinase receptor and vitronectin/alpha(v)beta(3) integrin induce chemotaxis and cytoskeleton reorganization through different signaling pathways," Oncogene, 2001, 20:2032-2043.
Ellis et al., J Biol Chem, "Plasminogen activation by receptor-bound urokinase. A kinetic study with both cell-associated and isolated receptor," 1991, 266:12752-12758.
Endsley et al., Maspin, the Molecular Bridge between the Plasminogen Activator System and beta-1 intergrin that Facilitates Cell Adhesion, J Biol Chem, 2011, 286(28):24599-24606.
Gao et al., "Maspin plays an essential role in early embryonic development," Development, 2004, 131:1479-1489.
Goldfinger et al., "Processing of laminin-5 and its functional consequences: role of plasmin and tissue-type plasminogen activator," J Cell Biol, 1998, 141:255-265.
Goldfinger et al., "The alpha3 laminin subunit, alpha6beta4 and alpha3beta1 integrin coordinately regulate wound healing in cultured epithelial cells and in the skin," J Cell Sci, 1999, 112(pt16):2615-2629.
Jo et al., "Soluble urokinase-type plasminogen activator receptor inhibits cancer cell growth and invasion by direct urokinase-independent effects on cell signaling," J Biol Chem, 2003, 278:46692-46698.
Khalkhali-Ellis and Hendrix, "Elucidating the function of secreted maspin: inhibiting cathepsin D-mediated matrix degradation," Cancer Res, 2007, 67:3535-3539.
Langhofer et al., "The matrix secreted by 804G cells contains laminin-related components that participate in hemidesmosome assembly in vitro," J Cell Sci, 1993, 105(Pt3):753-764.

(Continued)

*Primary Examiner* — Robert Landsman
*Assistant Examiner* — Bruce D Hissong
(74) *Attorney, Agent, or Firm* — Casimir Jones SC; David W. Staple

(57) ABSTRACT

The present invention provides maspin-related compositions and methods of use thereof. In particular, the present invention provides maspin-related compositions, and methods or use thereof, for the promotion of cell adhesion.

11 Claims, 8 Drawing Sheets

(56) References Cited

OTHER PUBLICATIONS

Law et al., "The high resolution crystal structure of the human tumor suppressor maspin reveals a novel conformational switch in the G-helix," J Biol Chem, 2005, 280:22356-22364.

McGowen et al., "The surface of prostate carcinoma DU145 cells mediates the inhibition of urokinase-type plasminogen activator by maspin," Cancer Res, 2000, 60:4771-4778.

Ma et al., "Regulation of Rac1 activation by the low density lipoprotein receptor-related protein," J Cell Biol, 2002, 159:1061-1070.

Maass et al., "Maspin—a novel protease inhibitor with tumor-suppressing activity in breast cancer," Acta Oncol, 2000, 39:931-934.

Madsen et al., "uPAR-induced cell adhesion and migration: vitronectin provides the key," J Cell Biol, 2007, 177:927-939.

Mazar et al., "The urokinase plasminogen activator system in cancer: Implications for tumor angiogenesis and metastasis," Angiogenesis, 1999, 3:15-32.

Ngamkitidechakul et al., "Maspin: synthesis by human cornea and regulation of in vitro stromal cell adhesion to extracellular matrix," Invest Ophthalmol Vis Sci, 2001, 42:3135-3141.

Nguyen et al., "Myosin light chain kinase functions downstream of Ras/ERK to promote migration of urokinase-type plasminogen activator-stimulated cells in an integrin-selective manner," J Cell Biol, 1999, 146:149-164.

Odero-Marah et al., "Maspin regulates different signaling pathways for motility and adhesion in aggressive breast cancer cells," Cancer Biol Ther, 2003, 2:398-403.

Pemberton et al., "Maspin is an intracellular serpin that partitions into secretory vesicles and is present at the cell surface," J Histochem Cytochem, 1997, 45:1697-1706.

Plopper et al., "Migration of breast epithelial cells on Laminin-5: differential role of integrins in normal and transformed cell types," Breast Cancer Res Treat, 1998, 51:57-69.

Qin & Zhang, "Maspin regulates endothelial cell adhesion and migration through an integrin signaling pathway," J Biol Chem, 2010, 285:32360-32369.

Ravenhill et al., "G-helix of maspin mediates effects on cell migration and adhesion," J Biol Chem, 2010, 285:36285-36292.

Seftor et al., "Maspin suppresses the invasive phenotype of human breast carcinoma," Cancer Res, 1998, 58:5681-5685.

Sheng et al., "Maspin acts at the cell membrane to inhibit invasion and motility of mammary and prostatic cancer cells," PNAS, 1996, 93:11669-11674.

Shi et al., "Blocking Tumor Growth, Invasion, and Metastasis by Maspin in a Syngeneic Breast Cancer Model," Cancer Res, 2001, 61:6945-6951.

Sidenius et al., "Shedding and cleavage of the urokinase receptor (uPAR): identification and characterisation of uPAR fragments in vitro and in vivo," FEBS Lett, 2000, 475:52-56.

Smith & Marshall, "Regulation of cell signalling by uPAR," Nat Rev Mol Cell Biol, 2010, 11:23-36.

Stoppelli et al., "Autocrine saturation of pro-urokinase receptors on human A431 cells," Cell, 1986, 45:675-684.

Tarui et al., "Urokinase-type plasminogen activator receptor (CD87) is a ligand for integrins and mediates cell-cell interaction," J Biol Chem, 2001, 276:3983-3990.

Tarui et al., "Critical role of integrin alpha 5 beta 1 in urokinase (uPA)/urokinase receptor (uPAR, CD87) signaling," J Biol Chem, 2003, 278:29863-29872.

Teoh et al., "Maspin (SERPINB5) is an obligate intracellular serpin," J Biol Chem, 2010, 285:10862-10869.

Uniprot P36952 SPB5_Human, retrieved May 16, 2012 (5 pages).

Wei et al., "Regulation of integrin function by the urokinase receptor," Science, 1996, 273:1551-1555.

Wei et al., J Cell Biol, "A role for caveolin and the urokinase receptor in integrin-mediated adhesion and signaling," 1999, 144:1285-1294.

Wei et al., "Regulation of alpha5beta1 integrin conformation and function by urokinase receptor binding," J Cell Biol, 2005, 168:501-511.

Willhelm et al., "Cellular glycosylphosphatidylinositol-specific phospholipase D regulates urokinase receptor shedding and cell surface expression," J Cell Physiol, 1999, 180:225-235.

Yerba et al., "Urokinase-type plasminogen activator binding to its receptor stimulates tumor cell migration by enhancing integrin-mediated signal transduction," Exp Cell Res, 1999, 250:231-240.

Yin et al., "Maspin retards cell detachment via a novel interaction with the urokinase-type plasminogen activator/urokinase-type plasminogen activator receptor system," Cancer Res, 2006, 66:4173-4181.

Zhang et al., "Maspin plays an important role in mammary gland development," Dev Biol, 1999, 215:278-287.

Zhang et al., "mMaspin: the mouse homolog of a human tumor suppressor gene inhibits mammary tumor invasion and motility," Mol Med, 1997, 3:49-59.

Zhang et al., "Maspin is an angiogenesis inhibitor," Nat Med, 2000, 6:196-199.

Zhang et al., "Reduced mammary tumor progression in WAP-TAg/WAP-maspin bitransgenic mice," Oncogene, 2000, 19:6053-6058.

Zou et al., "Maspin, a serpin with tumor-suppressing activity in human mammary epithelial cells," Science, 1994, 263:526-529.

Mickle et al., "Genotype-phenotype relationships in cystic fibrosis," Medical Clinics of North America, 2000, 84:597-607.

Wells, "Additivity of mutational effects in proteins," Biochemistry, 1990, 29:8509-8517.

SEQUENCE LISTING

```
<160> NUMBER OF SEQ ID NOS: 13

<210> SEQ ID NO 1
<211> LENGTH: 13
<212> TYPE: PRT
<213> ORGANISM: Homo sapiens

<400> SEQUENCE: 1

Thr Asp Thr Lys Pro Val Gln Met Met Asn Met Glu Ala
1               5                   10

<210> SEQ ID NO 2
<211> LENGTH: 10
```

```
<212> TYPE: PRT
<213> ORGANISM: Homo sapiens

<400> SEQUENCE: 2

Ala Asn Ala Lys Val Lys Leu Ser Ile Pro
1               5                   10

<210> SEQ ID NO 3
<211> LENGTH: 16
<212> TYPE: PRT
<213> ORGANISM: Homo sapiens

<400> SEQUENCE: 3

Asn Pro Ser Thr Met Ala Asn Ala Lys Val Lys Leu Ser Ile Pro Lys
1               5                   10                  15

<210> SEQ ID NO 4
<211> LENGTH: 23
<212> TYPE: PRT
<213> ORGANISM: Homo sapiens

<400> SEQUENCE: 4

Thr Asp Thr Lys Pro Val Gln Met Met Asn Met Glu Ala Thr Phe Cys
1               5                   10                  15

Met Gly Asn Ile Asp Ser Ile
            20

<210> SEQ ID NO 5
<211> LENGTH: 12
<212> TYPE: PRT
<213> ORGANISM: Homo sapiens

<400> SEQUENCE: 5

Ser Thr Ala Asn Ala Lys Val Lys Leu Ser Ile Pro
1               5                   10

<210> SEQ ID NO 6
<211> LENGTH: 12
<212> TYPE: PRT
<213> ORGANISM: Homo sapiens

<400> SEQUENCE: 6

Thr Ala Asn Ala Glu Val Lys Leu Ser Ile Pro Lys
1               5                   10

<210> SEQ ID NO 7
<211> LENGTH: 12
<212> TYPE: PRT
<213> ORGANISM: Homo sapiens

<400> SEQUENCE: 7

Ser Thr Glu Asn Ala Lys Val Lys Leu Ser Ile Pro
1               5                   10

<210> SEQ ID NO 8
<211> LENGTH: 40
<212> TYPE: DNA
<213> ORGANISM: Artificial sequence
<220> FEATURE:
<223> OTHER INFORMATION: DNA primer

<400> SEQUENCE: 8
ggatgaagaa atttccggca ttagaaccaa aagaatgtcc                           40
```

```
<210> SEQ ID NO 9
<211> LENGTH: 40
<212> TYPE: DNA
<213> ORGANISM: Artificial sequence
<220> FEATURE:
<223> OTHER INFORMATION: DNA primer

<400> SEQUENCE: 9
ggacattctt ttggttctaa tgccggaaat ttcttcatcc                              40

<210> SEQ ID NO 10
<211> LENGTH: 30
<212> TYPE: DNA
<213> ORGANISM: Artificial sequence
<220> FEATURE:
<223> OTHER INFORMATION: DNA primer

<400> SEQUENCE: 10
gatgaatctt aaggccactt tctgcttggg                                         30

<210> SEQ ID NO 11
<211> LENGTH: 30
<212> TYPE: DNA
<213> ORGANISM: Artificial sequence
<220> FEATURE:
<223> OTHER INFORMATION: DNA primer

<400> SEQUENCE: 11
cccaagcaga aagtggcctt aagattcatc                                         30

<210> SEQ ID NO 12
<211> LENGTH: 30
<212> TYPE: DNA
<213> ORGANISM: Artificial sequence
<220> FEATURE:
<223> OTHER INFORMATION: DNA primer

<400> SEQUENCE: 12
ggccaatgcc gaagtcgaac tttccctccc                                         30

<210> SEQ ID NO 13
<211> LENGTH: 30
<212> TYPE: DNA
<213> ORGANISM: Artificial sequence
<220> FEATURE:
<223> OTHER INFORMATION: DNA primer

<400> SEQUENCE: 13
gggagggaaa gttcgacttc ggcattggcc                                         30
```

MASPIN-BASED TREATMENT OF CANCER

CROSS-REFERENCE TO RELATED INFORMATION

The present invention is a divisional of U.S. patent application Ser. No. 13/478,904, filed May 23, 2012, now U.S. Pat. No. 8,791,233, which claims the benefit of U.S. Provisional Application Ser. No. 61/489,514, filed May 24, 2011, each of which are incorporated by reference in their entireties.

STATEMENT REGARDING GOVERNMENT FUNDING

This invention was made with government support under grant number R01 CA079736 awarded by the National Institutes of Health. The government has certain rights in the invention.

FIELD OF THE INVENTION

The present invention provides compositions and methods for the treatment of prevention of cancer through enhanced cell adhesion. In particular the present invention provides maspin-related compositions, and methods or use thereof, for the promotion of cell adhesion.

BACKGROUND

Maspin is a non-inhibitory serine protease inhibitor (serpin) that was originally identified as a type II tumor suppressor protein in mammary epithelial cells (Zou et al. (1994) Science 263, 526-529; herein incorporated by reference in its entirety). One major tumor suppressor function of maspin is suppression of tumor cell motility, since it inhibits tumor cell migration/invasion in vitro and suppresses metastasis in mouse models (Zou et al. (1994) Science 263, 526-529; Abraham et al. (2003) J Urol 169, 1157-1161; Seftor et al. (1998) Cancer Res 58, 5681-5685; Shi et al. (2001) Cancer Res 61, 6945-6951; Shi et al. (2002) Mol Ther 5, 755-761; Zhang et al. (1997) Mol Med 3, 49-59; Zhang et al. (2000) Oncogene 19, 6053-6058; herein incorporated by reference in their entireties). Several studies show that pericellular maspin inhibits cell motility by enhancing cell adhesion (Abraham et al. (2003) J Urol 169, 1157-1161; Seftor et al. (1998) Cancer Res 58, 5681-5685; Ngamkitidechakul et al. (2001) Invest Ophthalmol Vis Sci 42, 3135-3141; Cella et al. (2006) Faseb J 20, 1510-1512; herein incorporated by reference in their entireties). In addition to its tumor suppressing functions, maspin is also essential for normal fetal development since maspin knockout mice are embryonic lethal during the peri-implantation stage partially due to disrupted visceral endodermal cell adhesion (Gao et al. (2004) Development 131, 1479-1489; herein incorporated by reference in its entirety).

SUMMARY OF THE INVENTION

In some embodiments, the present invention provides a method of enhancing cell adhesion comprising administering a pro-adhesion protein or peptide to cells, tissue, or a subject. In some embodiments, enhancing cell adhesion results in reduced cell motility. In some embodiments, the cells, tissue, or subject comprise cancer cells, cells at risk of becoming cancerous, or cells at risk of metastasis. In some embodiments, the protein or peptide has at least 70% sequence (e.g., 70% . . . 80% . . . 90% . . . 95% . . . 98% . . . 99%) identity with all or a portion of wild-type maspin. In some embodiments, the protein or peptide has at least 70% sequence (e.g., 70% . . . 80% . . . 90% . . . 95% . . . 98% . . . 99%) identity with all or a portion of a mutant maspin. In some embodiments, the protein or peptide has at least 70% sequence (e.g., 70% . . . 80% . . . 90% . . . 95% . . . 98% . . . 99%) with a portion of maspin that is at least 6 amino acids in length (e.g., 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids . . . 30 amino acids . . . 40 amino acids, or more).

In some embodiments, the protein or peptide is capable of physically associating with uPAR, β1 integrin, or both. In some embodiments, the protein or peptide localizes at the cell surface upon administration to the cells, tissue, or a subject. In some embodiments, the protein or peptide co-localizes with the uPA/uPAR complex.

In some embodiments, the protein or peptide comprises a region with 70% sequence identity (e.g., 70% . . . 80% . . . 90% . . . 95% . . . 98% . . . 99%) with SEQ ID NO:1 (TDTKPVQMMNMEA). In some embodiments, the protein or peptide comprises a region with 70% sequence identity (e.g., 70% . . . 80% . . . 90% . . . 95% . . . 98% . . . 99%) with SEQ ID NO:2 (ANAKVKLSIP). In some embodiments, the protein or peptide comprises a region with 70% sequence identity (e.g., 70% . . . 80% . . . 90% . . . 95% . . . 98% . . . 99%) with SEQ ID NO:3 (NPSTMANAKVKLSIPK). In some embodiments, the protein or peptide comprises a region with 70% sequence identity (e.g., 70% . . . 80% . . . 90% . . . 95% . . . 98% . . . 99%) with SEQ ID NO:4 (TDTKPVQMMNMEATFCMGNIDSI). In some embodiments, the protein or peptide comprises a region with 70% sequence identity (e.g., 70% . . . 80% . . . 90% . . . 95% . . . 98% . . . 99%) with SEQ ID NO:5 (STANAKVKLSIP). In some embodiments, the protein or peptide comprises a region with 70% sequence identity (e.g., 70% . . . 80% . . . 90% . . . 95% . . . 98% . . . 99%) with SEQ ID NO:6 (TANAEVKLSIPK). In some embodiments, the protein or peptide comprises a region with 70% sequence identity (e.g., 70% . . . 80% . . . 90% . . . 95% . . . 98% . . . 99%) with SEQ ID NO:7 (STENAKVKLSIP).

In some embodiments, the present invention provides a composition comprising a peptide with at least 70% sequence identity with SEQ ID NO:1, SEQ ID NO:2, SEQ ID NO:3, SEQ ID NO:4, SEQ ID NO:5, SEQ ID NO:6 and/or SEQ ID NO:7, wherein the peptide enhances cell adhesion when administered to cells, tissue, or a subject.

In some embodiments, the present invention provides a pharmaceutical composition comprising: (a) a protein or peptide with at least 70% sequence identity with all or a portion of wild-type maspin, and (b) a physiologically suitable buffer. In some embodiments, the protein or peptide with at least 70% sequence identity with all or a portion of wild-type maspin enhances cell adhesion when administered to cells, tissue, or a subject. In some embodiments, all or a portion of the protein or peptide comprises at least 70% sequence identity with one or more of SEQ ID NO:1, SEQ ID NO: 2, SEQ ID NO:3, SEQ ID NO:4, SEQ ID NO:5, SEQ ID NO:6, and/or SEQ ID NO:7.

In some embodiments, the present invention provides a pharmaceutical composition comprising: (a) a peptide with at least 70% sequence identity with SEQ ID NO:1; (b) a peptide with at least 70% sequence identity with SEQ ID NO:2; and (c) a physiologically suitable buffer. In some embodiments, the pharmaceutical composition enhances cell adhesion when administered to cells, tissue, or a subject.

In some embodiments, the present invention provides a pharmaceutical composition comprising: (a) one or more of: (i) a peptide with at least 70% sequence identity with SEQ ID NO:1, (ii) a peptide with at least 70% sequence identity with SEQ ID NO:2, (iii) a peptide with at least 70% sequence identity with SEQ ID NO:3, (iv) a peptide with at least 70% sequence identity with SEQ ID NO:4, (v) a peptide with at least 70% sequence identity with SEQ ID NO:5, (vi) a peptide with at least 70% sequence identity with SEQ ID NO:6; (vii) a peptide with at least 70% sequence identity with SEQ ID NO:7; and (b) a physiologically suitable buffer. In some embodiments, the pharmaceutical composition enhances cell adhesion when administered to cells, tissue, or a subject.

In some embodiments, the present invention provides a method of treating or preventing cancer or metastasis comprising administering to a cell, tissue, or subject a composition comprising a protein or peptide comprising at least 70% sequence identity with a or a portion of one or more of: SEQ ID NO:1, SEQ ID NO:2, SEQ ID NO:3, SEQ ID NO:4, SEQ ID NO:5, SEQ ID NO:6, SEQ ID NO:7, or all or a portion of wild-type maspin, wherein administering the protein or peptide enhances cell adhesion and/or inhibits cell motility.

The present invention is not limited to treatment and/or prevention of cancer. The peptides provided herein also find use in treating other diseases and disorders. In certain embodiments, the present invention provides methods for treating bone formation disorders (e.g., by administration of peptides provided herein). In some embodiments, the methods comprise administering to a subject suffering from a bone formation disorder a composition comprising a protein or peptide comprising at least 70% sequence identity with a or a portion of one or more of: SEQ ID NO:1, SEQ ID NO:2, SEQ ID NO:3, SEQ ID NO:4, SEQ ID NO:5, SEQ ID NO:6, SEQ ID NO:7, or all or a portion of wild-type maspin. The methods are not limited to a particular type or severity of a bone formation disorder. An example of a bone formation disorder includes, but is not limited to, osteoporosis. The methods are not limited to treating a certain type of subject. In some embodiments, the subject is a rodent (e.g., mouse), while in other embodiments; the subject is a human being. In some embodiments, the composition is coadministered with, for example, an anti-osteoporosis agent (e.g., a hormone replacement therapy agent, a bisphosphonate (e.g., alendronate (e.g., FOSAMAX)), vitamin D, an androgen, a parathyroid hormone, a selective estrogen-receptor modulators, and a calcitonin-salmon). In certain embodiments, osteoblast cell proliferation is promoted by administering to a sample (or subject) comprising osteoblast cells a composition comprising a polypeptide or peptide comprising at least 70% sequence identity with a or a portion of one or more of: SEQ ID NO:1, SEQ ID NO:2, SEQ ID NO:3, SEQ ID NO:4, SEQ ID NO:5, SEQ ID NO:6, SEQ ID NO:7, or all or a portion of wild-type maspin.

DEFINITIONS

Figure 1:
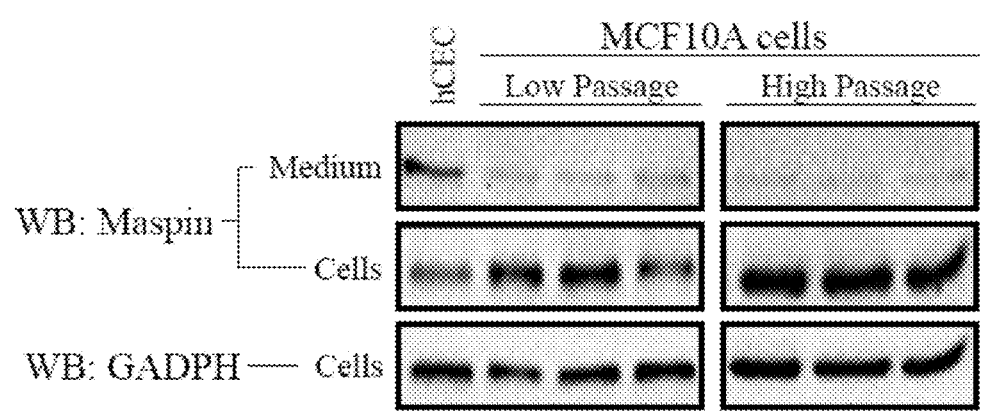
FIG. 1 shows images of Western blots demonstrating maspin release from MCF10A cells. Human corneal epithelial cells (hCEC), used as a control, or low and high passage MCF10A cells were maintained in defined keratinocyte serum free medium. Conditioned medium was collected, centrifuged to remove cell debris, and concentrated. Cells ($2\times10^6$) were solubilized with RIPA buffer containing protease inhibitors. Protein levels were measured by Pierce Coomassie Reagent and protein (20 µg) was run on 10% SDS-PAGE. Proteins in 50 ml of the 24× conditioned medium were separated on SDS-PAGE and visualized by Western blots using mouse anti-maspin (BD Biosciences) or rabbit anti-GAPDH (Chemicon).

As used herein, the term "subject" refers to any human or animal (e.g., non-human primate, rodent, feline, canine, bovine, porcine, equine, etc.). For methods of treatment, a subject may be any human or animal subject having a neoplasia, such as cancer or precancer. For methods of prevention, the subject may be any human or animal subject who is at risk of metastasis or developing a cancer. The subject may be at risk due to exposure to carcinogenic agents; being genetically predisposed to disorders characterized by unwanted, rapid cell proliferation; being predisposed (e.g., genetically or otherwise) to increased cell motility; etc. The term "patient" is used herein to refer to a human subject receiving treatment for a disease, disorder, and or condition, or being administered compositions of the present invention.

As used herein, the term "effective amount" refers to the amount of a composition (e.g., maspin-derived or maspin-related protein or peptide) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., compositions of the present invention) to a subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) (e.g., a combination maspin-derived or maspin-related proteins or peptides, a combination of oligonucleotides coding for a maspin-derived or maspin-related proteins or peptides, a maspin-related therapy and one or more other agents, etc.) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "pharmaceutical composition" refers to the combination of an active agent (e.g., maspin-derived or maspin-related protein or peptide) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

DETAILED DESCRIPTION OF THE INVENTION

The present invention provides compositions and methods for the treatment of prevention of cancer through enhanced cell adhesion. In particular the present invention provides maspin-related compositions, and methods or use thereof, for the promotion of cell adhesion.

Tumor metastasis involves recognition, degradation, and migration through the surrounding extracellular matrix (ECM), a process intrinsically dependent on cell-ECM adhesion. Many different proteins (and/or protein complexes) are involved in promoting or inhibiting tumor metastasis. Maspin is a tumor suppressing protein that is abundantly produced in normal mammary luminal epithelial and myoepithelial cells (Zou et al. (1994) *Science* 263, 526-529; herein incorporated by reference in its entirety). Upon tumor progression, maspin expression is significantly reduced or lost in breast and prostate carcinoma cell lines and tissues (Zou et al. (1994) *Science* 263, 526-529; Seftor et al. (1998) *Cancer Res* 58, 5681-5685; Zhang et al. (1997) *Mol Med* 3, 49-59; Sheng et al. (1996) *Proc Natl Acad Sci USA* 93, 11669-11674; herein incorporated by reference in their entireties). One of the major tumor suppressing functions of maspin is its ability to inhibit tumor cell motility and invasiveness, which is partially mediated by enhancing cell adhesion. The region between amino acids residues 139-225 in maspin facilitates increased mammary luminal epithelial (MCF10A) cell adhesion (Cella et al. (2006) *Faseb J* 20, 1510-1512; herein incorporated by reference in its entirety). Experiments conducted during development of embodiments of the present invention demonstrate (1) a unique region proximal to the reactive center loop (RCL) of maspin that mediates its adhesive function, and (2) identified a novel maspin/uPA/uPAR/β1 integrin complex, which facilitates maspin-mediated cell adhesion. Experiments conducted during development of embodiments of the present invention implicate maspin as an integrator of the urokinase activation system and integrin receptors by which cell adhesion and migration are regulated. Two different regions were identified proximal to the RCL of maspin that are responsible for maspin-mediated MCF10A cell adhesion. Enhanced adhesion was found to be dependent on the presence of both uPA and uPAR and is present in a complex with uPA/uPAR/β1 integrin on the cell surface. Together, experiments conducted during development of the present invention indicate that maspin coordinates both uPA/uPAR and β1 integrin receptors to regulate both mammary epithelial cell-ECM adhesion and migration.

Exogenous maspin treatment elicits similar anti-migratory effects seen in breast carcinoma cells overexpressing maspin cDNA (Seftor et al. (1998) *Cancer Res* 58, 5681-5685; Sheng et al. (1996) *Proc Natl Acad Sci USA* 93, 11669-11674; herein incorporated by reference in their entireties). These findings indicate that both endogenous and exogenous maspin act similarly at an extracellular site or are transported into an intracellular site of action. Studies suggest that maspin is secreted or present/associated at the cell surface (Seftor et al. (1998) *Cancer Res* 58, 5681-5685; Ngamkitidechakul et al. (2001) *Invest Ophthalmol Vis Sci* 42, 3135-3141; Cella et al. (2006) *Faseb J* 20, 1510-1512; Bass et al. (2009) *J Biol Chem* 284, 27712-27720; Pemberton et al. (1997) *J Histochem Cytochem* 45, 1697-1706; Khalkhali-Ellis & Hendrix (2007) *Cancer Res* 67, 3535-3539; Sheng et al. (1996) *Proc Natl Acad Sci USA* 93, 11669-11674; Law et al. (2005) *J Biol Chem* 280, 22356-22364; herein incorporated by reference in their entireties). However, recent data refutes these claims stating that maspin expression is absent from the surface of MCF10A cells and not secreted through the classical secretion pathway (Teoh et al. (2010) *J Biol Chem* 285, 10862-10869; herein incorporated by reference in its entirety). Confocal microscopy has been used to demonstrate that maspin is present on MCF10A cell surface and mediates adhesion (Cella et al. (2006) *Faseb J* 20, 1510-1512). Experiments were conducted during development of embodiments to clarify prior conflicting results on the presence of maspin at the cell surface. Since expression of maspin in human coronary stromal cells is reduced to undetectable levels in upon culturing (Ngamkitidechakul et al. (2001) *Invest Ophthalmol Vis Sci* 42, 3135-3141; herein incorporated by reference in its entirety), it was investigated whether maspin secretion is lost as a result of culturing conditions. The detection of maspin protein, by Western immunoblot, is reduced in media obtained from high passage MCF10A cells when compared to low passage cells. Additionally, no significant difference was detected between cellular maspin expressions in the high versus low passage MCF10A cells. These data indicate that extracellular maspin detection is lost depending on culturing conditions; thereby providing an explanation for previous conflicting results.

Experiments were conducted during development of embodiments of the present invention to determine the region involved in maspin-mediated cell adhesion. Several peptides were generated from the 139-225 region of maspin. The crystal structure of maspin reveals several structural motifs within this region including the third strand of the A β-sheet (s3A), third strand of the C β-sheet (s3C), and first strand of the B β-sheet (s1B) (Law et al. (2005) *J Biol Chem* 280, 22356-22364; Al-Ayyoubi et al. (2004) *J Biol Chem* 279, 55540-55544; herein incorporated by reference in its entirety). Due to the presence of surface-exposed amino acid side chains, s3C and s1B (amino acids 180-210) were tested for adhesion effects. Experiments indicated that s1B (peptides 181-202 and 190-211) not s3C (peptide 169-189) was important in mediating cell adhesion. Moreover, a point mutation (E201K) within this region significantly reduced MCF10A cell adhesion. Experiments indicate that the amino acids overlapping these peptides, amino acids 190-202 (TDTKPVQMMNMEA; SEQ ID NO:1) in maspin are integral for maspin-mediated cell adhesion. These amino acids are highly conserved between human, mouse, rat, and chicken species (84% sequence identity and 100% similarity), indicating their importance throughout evolution (Law et al. (2005) *J Biol Chem* 280, 22356-22364; incorporated herein by reference in its entirety).

Maspin inhibits prostate carcinoma cell migration and invasion due, at least in part, to the strengthening of mature focal adhesion contacts (Yin et al. (2006) *Cancer Res* 66, 4173-4181; herein incorporated by reference in its entirety). In addition, experiments conducted demonstrate that maspin binds uPA (and pro-uPA) and co-localizes with uPAR on the cell surface (Yin et al. (2006) *Cancer Res* 66, 4173-4181; McGowen et al. (2000) *Cancer Res* 60, 4771-4778; Biliran & Sheng. (2001) *Cancer Res* 61, 8676-8682; herein incorporated by reference in their entireties). Maspin binding does not directly inhibit uPA proteolytic activity but rather binds to uPA (and pro-uPA) via a region of maspin in close proximity to the RCL (Al-Ayyoubi et al. (2007) *J Biol Chem* 282, 19502-19509; Bass et al. (2002) *J Biol Chem* 277, 46845-46848; herein incorporated by reference in their entireties). Experiments conducted during development of the present invention demonstrated that the RCL is in close proximity to the s1B (191-211) region of maspin. Another region, s2C (SEQ ID NO:2; residues 265-274; ANAKVKL-SIP), is also proximal to both the RCL and s1B. Experiments conducted during development of embodiments of the present invention demonstrated that the s1B region is important in mediating cell adhesion. Moreover, the 260-275 peptide (SEQ ID NO:3; NPSTMANAKVKLSIPK) and double mutant GST maspin (K268E, K270E) reduced MCF10A cell adhesion compared to wild-type GST-maspin. Experiments using the triple mutant maspin (E201K, K268E, K270E) verified that both regions are important for cell adhesion. These findings indicate that the s1B and s2C regions of maspin facilitate cell adhesion.

Experiments were conducted during development of embodiments of the present invention to identify dependence of maspin-mediated cell adhesion on the plasminogen activation pathway. Removal of endogenous uPA from the surface of MCF10A cells abrogated maspin-mediated adhesion. However, administration of exogenous uPA restored maspin-mediated cell adhesion in a concentration-dependent manner. These results indicate that that exogenous (or cell surface localized) uPA expression is necessary for the proadhesion function of maspin.

Localization of uPA to cell-cell contacts and focal adhesions is mediated by its receptor, uPAR. The uPA/uPAR interaction is very tight with binding affinities in the low nanomolar range. Extracellular maspin expression is localized to the cell surface (Abraham et al. (2003) *J Urol* 169, 1157-1161; Yin et al. (2006) *Cancer Res* 66, 4173-4181; Biliran & Sheng. (2001) *Cancer Res* 61, 8676-8682; Pemberton et al. (1997) *J Histochem Cytochem* 45, 1697-1706; herein incorporated by reference in their entireties). Experiments conducted during development of embodiments of the present invention to evaluate the binding of exogenous maspin to wild type (WT) or uPAR−/− mouse embryo fibroblast (MEFs) found maspin localized on the surface of WT MEFs, but did not detect maspin expression on the surface of uPAR−/− MEFs. These results indicate that maspin binds to uPA (and potentially pro-uPA) and is localized to the cell surface by maspin/uPA binding to uPAR. Experiments were conducted to confirm the importance of the uPA/uPAR complex in facilitating maspin-mediated cell adhesion by: (1) stripping uPA from the surface of MCF10A cells, (2) disrupting the uPA/uPAR binding with an antibody, and (3) testing MCF10A cell adhesion after uPA and GST-maspin were added. These experiments demonstrated that if uPA is blocked from binding to uPAR, the increased MCF10A cell adhesion mediated by maspin is significantly reduced. Alternatively, if uPA is not stripped from the cell surface and the uPAR antibody is added, no effect in adhesion was detected. These results indicate that maspin localization to the cell surface and function on cell adhesion is based on the uPA/uPAR complex. As such, altered cell surface expression of uPA or uPAR will result in altered maspin localization and cell adhesion. For instance, cells under siege from increased phospholipase and protease activity liberate uPAR from its GPI membrane tether (Sidenius et al. (2000) *FEBS Lett* 475, 52-56; Wilhelm et al. (1999) *J Cell Physiol* 180, 225-235; herein incorporated by reference in their entireties).

Experiments conducted during development of the present invention demonstrate that maspin produces a novel coordination of the plasminogen activation system and integrin receptors, which is necessary to facilitate its anti-migratory ability. The s1B and s2C regions (amino acid residues 190-202 and 260-275, respectively) of maspin are responsible for its effects on cell adhesion and the necessity of the uPA/uPAR complex for this effect. The ability of maspin to integrate into this signaling complex is retained even in tumor cells, as recombinant maspin still facilitates anti-migratory signaling even after its expression is lost (Zou et al. (1994) *Science* 263, 526-529; Seftor et al. (1998) *Cancer Res* 58, 5681-5685; Sheng et al. (1996) *Proc Natl Acad Sci USA* 93, 11669-11674; Sheng et al. (1996) *Proc Natl Acad Sci USA* 93, 11669-11674; Zhang et al. (1999) *Dev Biol* 215, 278-287; herein incorporated by reference in their entireties).

In some embodiments, the present invention provides compositions, kits, systems, and/or methods to treat or prevent cancer, metastatasis, or unusual cell motility. In some embodiments, the present invention enhances cell adhesion and/or prevents cell motility. In some embodiments, cell adhesion is enhanced in cells undergoing metastasis or at risk of entering metastasis. In some embodiments, cell adhesion is enhanced in neoplastic cells (e.g., cancerous, pre-cancerous). In some embodiments, compositions and methods are utilized in the treatment and/or prevention of: bladder cancer, lung cancer, breast cancer, melanoma, colon and rectal cancer, non-Hodgkin lymphoma, endometrial cancer, pancreatic cancer, kidney (renal cell) cancer, prostate cancer, leukemia, thyroid cancer, and/or metastasis thereof. In some embodiments, the present invention enhances cell adhesion and/or inhibits cell motility in non-neoplastic or non-cancerous cells.

In some embodiments, the present invention provides a pharmaceuticals, small molecules, peptides, proteins, polypeptides, nucleic acids, molecular complexes, etc. for the treatment or prevention of cancer (e.g., metastasis), enhancement of cell adhesion, and/or inhibition of cell motility. In some embodiments, the present invention provides administration of a maspin-based peptide (e.g., polypeptide comprising: full length maspin, SEQ ID NO:1, SEQ ID NO:2, SEQ ID NO:3, SEQ ID NO:4, SEQ ID NO:5, SEQ ID NO:6, SEQ ID NO:7, etc.) to inhibit cell motility and/or enhance cell adhesion. In some embodiments, a polypeptide of the present invention can be prepared by methods known to those of ordinary skill in the art. For example, the claimed polypeptide can be synthesized using solid phase polypeptide synthesis techniques (e.g. Fmoc). Alternatively, the polypeptide can be synthesized using recombinant DNA technology (e.g., using bacterial or eukaryotic expression systems). Accordingly, to facilitate such methods, the present invention provides genetic vectors (e.g., plasmids) comprising a sequence encoding the inventive polypeptide, as well as host cells comprising such vectors. Furthermore, the invention provides the polypeptide produced via recombinant methods.

In some embodiments, the present invention provides administration of maspin-based (e.g., maspin-related, maspin-derived, etc.) compositions (e.g. maspin, maspin-based peptides, mimetics of maspin, nucleic acids encoding maspin-based peptides, etc.). In some embodiments, the present invention provides administration of polypeptides which inhibit cell motility (e.g. maspin, SEQ ID NO:1, SEQ ID NO:2, SEQ ID NO:3, SEQ ID NO:4, SEQ ID NO:5, SEQ ID NO:6, SEQ ID NO:7, combinations thereof, derivatives thereof, etc.). In some embodiments, the present invention provides administration of nucleic acids which encode polypeptides motility (e.g. maspin, SEQ ID NO:1, SEQ ID NO:2, SEQ ID NO:3, SEQ ID NO:4, SEQ ID NO:5, SEQ ID NO:6, SEQ ID NO:7, combinations thereof, derivatives thereof, etc.) which inhibit cell motility and/or enhance cell adhesion. In some embodiments, a polypeptide comprising or consisting of SEQ ID NO:1 is administered. In some embodiments, a polypeptide comprising or consisting of SEQ ID NO:2 is administered. In some embodiments, a polypeptide comprising or consisting of SEQ ID NO:3 is administered. In some embodiments, a polypeptide comprising or consisting of SEQ ID NO:4 is administered. In some embodiments, a polypeptide comprising or consisting of SEQ ID NO:5 is administered. In some embodiments, a polypeptide comprising or consisting of SEQ ID NO:6 is administered. In some embodiments, a polypeptide comprising a portion with at least 50% homology to SEQ ID NO:1, SEQ ID NO:2, SEQ ID NO:3, SEQ ID NO:4, SEQ ID NO:5, SEQ ID NO:6, and/or SEQ ID NO:7 is administered (e.g. at least 60% homology, at least 70% homology, at least 80% homology, at least 90% homology, at least 95% homology, at least 99% homology, etc.). In some embodiments, administering a maspin-based peptide, nucleic acid, or a drug-like small molecule to a subject or cell inhibits pathways related to cell-motility, inhibits cell motility, and/or protects against undesired cell motility.

A modified peptide can be produced in which the nucleotide sequence encoding the polypeptide has been altered, such as by substitution, deletion, or addition. In particularly preferred embodiments, these modifications do not significantly reduce the biological activity of the modified maspin peptides. In other words, construct "X" can be evaluated in order to determine whether it is a member of the genus of modified or variant maspin's of the present invention as defined functionally, rather than structurally. In preferred embodiments, the activity of variant maspin polypeptides is evaluated by methods described herein. In some embodiments, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of maspin containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (see, e.g., Stryer ed., Biochemistry, pg. 17-21, 2nd ed, WH Freeman and Co., 1981; herein incorporated by reference in its entirety). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

In some embodiments, polypeptides of the present invention are isolated and/or purified (or substantially isolated and/or substantially purified). Accordingly, the invention provides polypeptide in substantially isolated form. In some embodiments, polypeptides are isolated from other polypeptides as a result of solid phase protein synthesis, for example. Alternatively, polypeptides can be substantially isolated from other proteins after cell lysis from recombinant production. Standard methods of protein purification (e.g., HPLC) can be employed to substantially purify polypeptides. In some embodiments, the present invention provides a preparation of polypeptides in a number of formulations, depending on the desired use. For example, where the polypeptide is substantially isolated (or even nearly completely isolated from other proteins), it can be formulated in a suitable medium solution for storage (e.g., under refrigerated conditions or under frozen conditions). Such preparations may contain protective agents, such as buffers, preservatives, cryprotectants (e.g., sugars such as trehalose), etc. The form of such preparations can be solutions, gels, etc., and the inventive polypeptide can, in some embodiments, be prepared in lyophilized form. Moreover, such preparations can include other desired agents, such as small molecules or even other polypeptides and proteins, if desired. Indeed, the invention provides such a preparation comprising a mixture of different embodiments of the inventive polypeptide (e.g., a plurality of polypeptide species as described herein).

In some embodiments, the present invention also provides a pharmaceutical composition comprising of one or more polypeptides (full-length maspin or portion thereof, polypeptides comprising SEQ ID NO:1, SEQ ID NO:2, SEQ ID NO:3, SEQ ID NO:4, SEQ ID NO:5, and/or SEQ ID NO:6, mixtures thereof, derivatives thereof, mutants thereof, etc.) and a pharmaceutically acceptable carrier. Any carrier which can supply a polypeptide without destroying the vector within the carrier is a suitable carrier, and such carriers are well known in the art. The composition can be formulated for parenteral, oral, or topical administration. For example, a parenteral formulation could consist of a prompt or sustained release liquid preparation, dry powder, emulsion, suspension, or any other standard formulation. An oral formulation of the pharmaceutical composition could be, for example, a liquid solution, such as an effective amount of the composition dissolved in diluents (e.g., water, saline, juice, etc.), suspensions in an appropriate liquid, or suitable emulsions. An oral formulation could also be delivered in tablet form, and could include excipients, colorants, diluents, buffering agents, moistening agents, preservatives, flavoring agents, and pharmacologically compatible excipients. A topical formulation could include compounds to enhance absorption or penetration of the active ingredient through the skin or other affected areas, such as dimethylsulfoxide and related analogs. The pharmaceutical composition could also be delivered topically using a transdermal device, such as a patch, which could include the composition in a suitable solvent system with an adhesive system, such as an acrylic emulsion, and a polyester patch. Compositions could be delivered via eye drops or other topical eye delivery method. Compositions may be delivered intraocularly, anywhere in the eye including, for example, the vitreous cavity, the anterior chamber, etc. Compositions may be delivered intravitrealy as is commonly done with intravitreal injections of Lucentis (ranabizumab), Avastin (bevazizumab), triamcinolone acetonide, antibiotics, etc. Compositions may be administered using encapsulated cell technology (e.g. by Neurotech) in which genetically modified cells are engineered to produce and secrete compositions of the present invention (e.g. maspin-based proteins or peptides).

In some embodiments, the methods of the present invention are employed in vivo. In some embodiments, polypeptides are delivered to a human or animal subject in an amount and at a location sufficient to inhibit or attenuate cell motility or enhance cell adhesion within a population of cells (e.g., within desired tissue, within the patient, etc.). Polypeptide can be formulated into a suitable pharmaceutical composition (e.g., as described above or as otherwise known to those of ordinary skill in the art) for delivery into the subject. The delivery can be local (e.g., by injection or implantation within the desired tissue to be treated) or systemic (e.g., by intravenous or parenteral injection).

In some embodiments, the present invention provides a method for treating patients suffering from (or at risk of) neoplasia and in need of treatment (or preventative therapy). In some embodiments, a pharmaceutical composition comprising at least one polypeptide of the present invention is delivered to such a patient in an amount and at a location sufficient to treat the condition. In some embodiments, polypeptides of the present invention (or pharmaceutical composition comprising such) can be delivered to the patient systemically or locally, and it will be within the ordinary skill of the medical professional treating such patient to ascertain the most appropriate delivery route, time course, and dosage for treatment. It will be appreciated that application of the inventive method of treating a patient most preferably substantially alleviates or even eliminates such symptoms; however, as with many medical treatments, application of the inventive method is deemed successful if, during, following, or otherwise as a result of the inventive method, the symptoms of the disease or disorder in the patient subside to an ascertainable degree.

A pharmaceutical compound may be administered in the form of a composition which is formulated with a pharmaceutically acceptable carrier and optional excipients, adjuvants, etc. in accordance with good pharmaceutical practice. The maspin-based (e.g., comprising SEQ ID NO:1, SEQ ID NO:2, SEQ ID NO:3, SEQ ID NO:4, SEQ ID NO:5, SEQ ID NO:6 and/or SEQ ID NO:7, mixtures thereof, derivatives thereof, mutants thereof, etc.) pharmaceutical composition may be in the form of a solid, semi-solid or liquid dosage form: such as powder, solution, elixir, syrup, suspension, cream, drops, paste and spray. As those skilled in the art would recognize, depending on the chosen route of administration (e.g. pill, injection, etc.), the composition form is determined. In general, it is preferred to use a unit dosage form of the inventive inhibitor in order to achieve an easy and accurate administration of the active pharmaceutical compound. In general, the therapeutically effective pharmaceutical compound is present in such a dosage form at a concentration level ranging from about 0.5% to about 99% by weight of the total composition: i.e., in an amount sufficient to provide the desired unit dose. In some embodiments, the pharmaceutical composition may be administered in single or multiple doses. The particular route of administration and the dosage regimen will be determined by one of skill in keeping with the condition of the individual to be treated and said individual's response to the treatment. In some embodiments, a maspin-based pharmaceutical composition in a unit dosage form for administration to a subject, comprising a pharmaceutical compound (e.g., comprising SEQ ID NO:1, SEQ ID NO:2, SEQ ID NO:3, SEQ ID NO:4, SEQ ID NO:5, SEQ ID NO:6 and/or SEQ ID NO:7, mixtures thereof, derivatives thereof, mutants thereof, etc.) and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions.

In some embodiments, maspin-based compositions of the present invention are provided as part of a kit. In some embodiments, a kit of the present invention comprises one or more maspin-based compositions and/or maspin-based pharmaceutical compositions. In some embodiments, a kit comprises a maspin-based composition configured for co-administration with one or more additional compositions (e.g. pharmaceutical compositions). In some embodiments, one or more maspin-based compositions are co-administered with one or more other agents for effective enhancement of cell adhesion, inhibition of cell motility, and/or treatment or prevention of cancer or metastasis.

In some embodiments, maspin-related compositions are provided for the promotion of cell adhesion and/or inhibition of cell migration. However, the compositions and methods described herein are not limited by their particular application or field of use. In some embodiments, compositions and methods find use in the treatment and/or prevention of cancer, metastasis, or other neoplastic disorders of conditions. In some embodiments, compositions and methods find use in the treatment and/or prevention disorders associated with bone formation (e.g., osteoporosis), as is described for purified maspin in US Pat. App. 20090263363; herein incorporated by reference in its entirety. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

EXPERIMENTAL

Example 1

Materials and Methods

Antibodies and Reagents—

Rabbit antihuman uPAR (American Diagnostics) for immunoprecipitation (IP) and functional blocking experiments. Mouse monoclonal anti-maspin (Pharmingen) and rabbit polyclonal anti-β1 integrin (Chemicon) was used for both IP and immunoblot probing. An affinity-purified rabbit polyclonal antibody raised against maspin reactive center loop (RCL) peptide (AbS4A) was used from previous studies (Zou et al. (1994) Science 263, 526-529). Both the horseradish peroxidase-conjugated secondary antibodies and maspin peptides were obtained from Sigma-Aldrich. Human uPA was purchased from Chemicon.

Cell Culture—

MCF10A, immortalized human mammary luminal epithelial cells, (CRL-10317; American Type Culture Collection) were cultured in Dulbecco's modified Eagle medium (DMEM)/F12 (Invitrogen) containing 5% donor horse serum, 20 µg/ml epidermal growth factor (EGF), 100 µg/ml cholera toxin, 10 µg/ml insulin, 500 µg/ml hydrocortisone, 50 U/ml penicillin, and 50 µg/ml streptomycin at 37° C. and 5% $CO_2$. All growth factors and hormones were purchased from Sigma. For maspin secretion studies, MCF10A cells either directly ordered from ATCC (low passage) or carried in the lab for two years (high passage) were maintained in defined keratinocyte serum free medium (Invitrogen) supplemented with ciprofloxacin and MITO+ (BD Biosciences). Cells were passaged weekly and fed three times per week. Conditioned medium was collected on the day of passage, centrifuged to remove cell debris and concentrated 24× using a 30 kDa spin filter (Millipore). Harvested protein was then used for Western blot analysis, as described later. Control (uPAR+/+) and uPAR-deficient (uPAR−/−) murine embryonic fibroblasts (MEFs) were isolated from embryos as previously described (Ma et al. (2002) *J Cell Biol* 159, 1061-1070; herein incorporated by reference in its entirety).

Construction, Expression, and Purification of GST-Maspin and Mutants—

Glutathione Stransferase (GST)-tagged maspin (GST-maspin) was produced as previously described (Zhang et al. (2000) Nat Med 6, 196-199; herein incorporated by reference in its entirety). Point mutants were constructed with QuikChange Multi Site Directed Mutagenesis kit (Stratagene), according to manufacturer's instruction. The primers are as following: control mutant D177A, S178L, T180P (forward: 5'-GGATGAAGAAATTTCCGGCATTAGAAC-CAAAAGAATGTCC (SEQ ID NO: 8), reverse: 5'-GGA-CATTCTTTTGGTTCTAATGCCGGAAATTTCTTCATCC (SEQ ID NO: 9)); E201K mutant (forward: 5'-GAT-GAATCTTAAGGCCACTTTCTGCTTGGG (SEQ ID NO: 10), reverse: 5'-CCCAAGCAGAAAGTGGCCTTAAGAT-TCATC (SEQ ID NO: 11); K268E, K270E mutant (forward: 5'-GGCCAATGCCGAAGTCGAACTTTCCCTCCC (SEQ ID NO: 12); reverse: 5'-GGGAGGGAAAGTTCGACT-TCGGCATTGGCC (SEQ ID NO: 13)). To develop the triple mutant (E201K, K268E, K270E), primers of mutant K268E, K270E and E201K were used as the template. In order to verify their fidelity, the constructs were sequenced. The constructs were transformed into *E. coli* BL21 cells and expressed and purified, according to manufacturer's instructions (GE Healthcare).

Adhesion Assay—

Assays utilizing endogenous ECM proteins generated by MCF10A cells were performed as previously described (Langhofer et al. (1993) *J Cell Sci* 105 (Pt 3), 753-764; herein incorporated by reference in its entirety). MCF10A cells were plated in 96-well dishes and allowed to reach confluence. Cells were washed with PBS and treated for 5 min with fresh sterile 20 mM NH4OH, followed by extensive water washes. Wells were blocked with heat-denatured BSA (10 mg/ml) for 1 hr at room temperature. Subconfluent cultures were trypsinized, washed with 37° C. serum-free DMEM/F12 medium, and incubated with either antibodies or recombinant proteins (500 nM) for 30 min at 37° C. (when assaying endogenous maspin enzyme-free cell dissociation solution was used instead of trypsin). In all assays, 2.0×104 cells were plated in triplicates and allowed to adhere for 30 min at 37° C. The GST protein was used as a control. Wells were washed with 37° C. serum-free DMEM/F12 and adhered cells were fixed with 5% gluteraldehyde and stained with crystal violet dye. Cell adhesion was determined by the reading at 590 nm subtracted by the blank value (determined by BSA-coated wells, 5% of maximal cell adhesion). Cell adhesion was plotted as percentage of the corresponding control value. Cell surface stripping of uPA from uPAR was conducted as previously described (Stoppelli et al. (1986) *Cell* 45, 675-684; herein incorporated by reference in its entirety). Subconfluent cultures were washed twice with DMEM/F12 supplemented with 20 mM HEPES and 1 mg/ml BSA. Then, cells were incubated with 50 mM glycine-HCl (pH 3.0) with 100 mM NaCl at 25° C. for 2 min and the reaction was halted by neutralizing with 500 mM HEPES (pH 7.4). In the function blocking studies, cells were first incubated with the function blocking antiuPAR or control rabbit IgG for 10 min, uPA and recombinant GST-maspin was added for another 20 min.

Maspin Binding Assay—

Bacterial recombinant GST-maspin was labeled with $^{125}$I as described previously (Conlon, M. (2002) *Preparation of $^{125}$I-Labeled Peptides and Proteins with High Specific Activity using IODO-GEN*, 2nd Edition Ed. The Protein Protocols Handbook (Walker, J. M., Ed.), Humana Press Inc, Totowa, N.J.; herein incorporated by reference in its entirety). Wild type (WT) and uPAR−/− mouse embryo fibroblasts (MEFs) (5.0×104 cells) were cultured in DMEM with 10% FBS on 96-well plate overnight. Cells were chilled on ice for 30 min, washed three times with ice-cold DMEM, and then blocked on ice for 60 min using blocking buffer (DMEM containing 5% heat inactivated BSA). MEFs were incubated with increasing concentrations of $^{125}$I-GST-maspin in blocking buffer at 4° C. for 90 min. After incubation, unbound $^{125}$I-GST-maspin protein was removed by washing three times with blocking buffer. Specific $^{125}$I-GST-maspin binding was determined by subtracting the detected radioactivity by the nonspecific binding (determined in the presence of a 50-fold excess of non-labeled GST-maspin). In the studies evaluating the uPA/uPAR interactions, $^{125}$I-GST-maspin was treated with ABS4A and S-20 (Santa Cruz) antibodies, which block the RCL and N-terminal domains, prior to adding to WT MEF cells. In one set, WT MEF cells were treated with an anti-mouse uPAR antibody (R&D), which blocks uPA binding to uPAR. In the other set, WT MEF cells were stripped of uPA, then treated with the antimouse uPAR antibody, and then administered uPA (800 nM) and $^{125}$I-GST-maspin. Results were reported as $^{125}$I-GST-maspin binding to WT MEF cell surface as a percentage of control (IgG) antibody treatment.

Immunoprecipitation and Western Blot— uPAR was overexpressed in MCF10A cells. Lysates from MCF10A cells overexpressing uPAR were prepared in modified radio-immunoprecipitation assay (RIPA) buffer: 50 mM Tris (pH 7.4), 1% Triton X-100, 1% sodium deoxycolate, 150 mM NaCl, 5 mM EDTA (pH 8.0), 5 mM PMSF, and protease inhibitor cocktail (Thermo Scientific). Cellular debris was cleared from lysates by centrifugation and protein concentration was determined by the BCA Protein Assay (Pierce). Whole cell extracts (500 µg) were incubated overnight (constant rocking) with 5 µg of specific antisera or control rabbit irrelevant antiserum (Ki67) at 4° C. Protein A-Sepharose-coupled beads (Amersham Pharmacia Biotech) were added and incubated for 2 hr at 4° C. under constant agitation. Beads were centrifuged, washed three times with ice-cold lysis buffer, and boiled for 5 min in sample buffer containing 5% β-mercaptoethanol. Samples separated on SDS-PAGE gels, transferred to a PVDF membrane (GE Healthcare), and probed for β1 integrin, uPAR and maspin. Appropriate secondary antibodies were added and proteins were visualized with enhanced chemiluminescence substrate (Pierce).

Example 2

Maspin is Secreted/Released from Cells

MCF10A cells were tested to determine if maspin is secreted/released into culturing media. The culturing media was obtained from two different MCF10A populations; i) cells obtained directly from ATCC or ii) cells that have been cultured in the laboratory for two years, and analyzed by Western immunoblot for maspin protein expression. Maspin was detected in all media and cells tested (SEE FIG. 1A). Using densitometry analysis, it was determined that media from high passage MCF10A cells had reduced maspin expression compared to the media from low passage cells. However, cellular maspin expression did not statistically differ between low- and high-passage MCF10A. These results indicate that maspin is secreted/released from MCF10A cells and the loss of maspin secretion could be an artifact of extended cell culturing conditions.

Example 3

Figure 2:
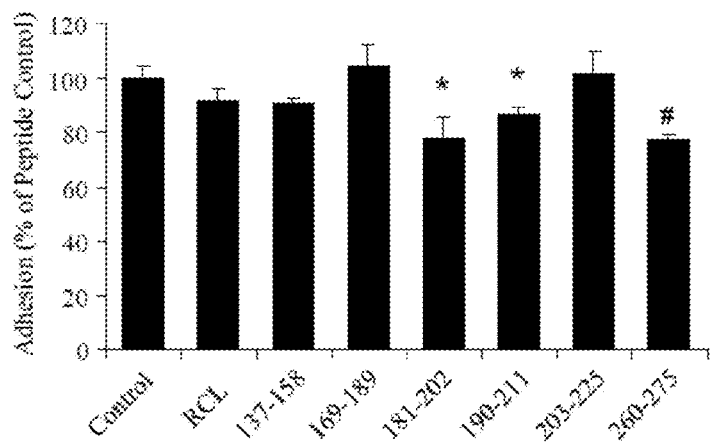
FIG. 2 shows graphs demonstrating that maspin-derived peptides and mutation of maspin (E201, K268, and/or K270) inhibits MCF10A cell adhesion to self-deposited matrix. (A) MCF10A cells were harvested with enzyme-free dissociation buffer, and pre-incubated with the indicated peptides. Cells ($2.0\times10^4$ cells) were seeded and adhesion was measured after 30 min using colorimetric reaction. Peptides 181-202, 190-211, and 260-275 inhibited cell adhesion whereas no significant effect was detected with other peptides. (B) Software Molsoft ICM-pro version 3.48 was used for 3D structure analysis of maspin. The amino acids E201 (blue), K268, K270 (green) are exposed on the surface of maspin. The control peptide is marked in red. (C) MCF10A cells ($2.0\times10^4$ cells) were incubated with GST, GST-maspin, or GSTmaspin mutants on endogenous matrix. Maspin mutants, E201K, double mutant (K268E, K270E), and triple mutant (E201K, K268E, K270E) inhibited cell adhesion.
Figure 2:
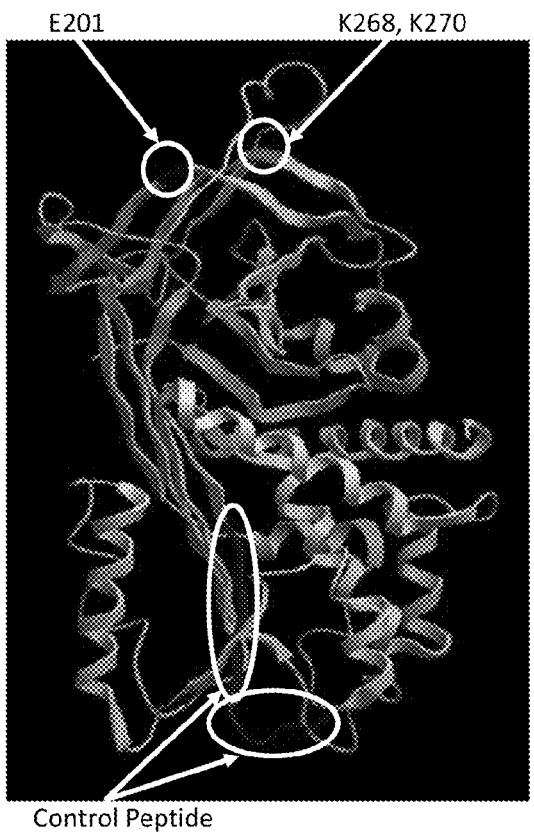
Figure 2:
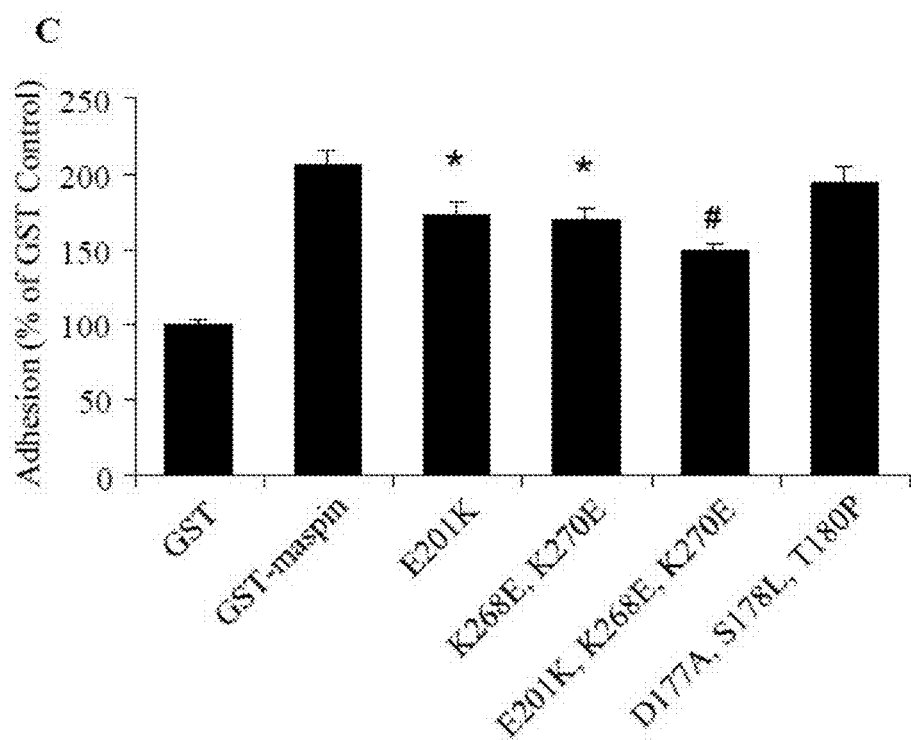

Two Proximal Sites to the Reactive Center Loop are Responsible for Cell Adhesion MCF10A cells deposit ECM proteins and can nucleate adhesive complexes typical of epithelia (Goldfinger et al. (1998) *J Cell Biol* 141, 255-265; Goldfinger et al. (1999) *J Cell Sci* 112 (Pt 16), 2615-2629; herein incorporated by reference in their entireties). To determine the region(s) of maspin that are involved in adhesion, competitive peptides were used. First, peptides were developed that dissect the aforementioned region (amino acid residues 139-225) into peptides corresponding to amino acid residues; 137-158, 169-189, 181-202, 190-211, and 203-225. Then, using Molsoft ICM software to analyze the tertiary structure of maspin, peptides were developed to other regions of maspin that are exposed such as the RCL (329-343), 260-275 and the control peptide (97-112). Using these peptides, the regions of maspin involved in mediating MCF10A cell adhesion were determined. The only peptides (derived from amino acid residues 139-225) that competed with GST-maspin were the 181-202 and 190-211 (SEQ ID NO:4; TDTK-PVQMMNMEATFCMGNIDSI) peptides (SEE FIG. 2A). These results have identified the 190-202 region of maspin is partially responsible for mediating cell adhesion. In addition, a novel region between amino acids 260-275 was identified that is also important in regulating maspin-mediated MCF10A cell adhesion (SEE FIG. 1A). Although the 190-202 and 260-275 peptides are separated by 58 amino acids in the primary structure of maspin, they are adjacent to one another in the tertiary structure (SEE FIG. 2B).

To further demonstrate that these regions are involved in maspin-mediated adhesion, mutants of GST-maspin were developed; single mutant (E201K), double mutant (K268E, K270E), triple mutant (E201K, K268E, K270E) and a control mutant (D177A, S178L, T180P). The single (E201K) mutant corresponds to peptide 181-202 while the double (K268E, K270E) mutant corresponds to peptide 260-275. The control (D177A, S178L, T180P) mutant failed to have any reduced cell adhesion. However, both the single and double GST-maspin mutants had significantly reduced MCF10A cell adhesion (by 16% and 17%, respectively), as compared to WT GST-maspin (SEE FIG. 1C). The triple (E201K, K268E, K270E) mutant had an additive effect whereby MCF10A cell adhesion was decreased by approximately 28% when compared to WT GST-maspin (SEE FIG. 2C). These findings demonstrate that proximal amino acid residues from 190-202 and 260-275 in maspin mediate its effect on MCF10A cell adhesion.

Example 4

Maspin Localization to the Cell Surface Requires the uPA/uPAR Complex

Figure 3:
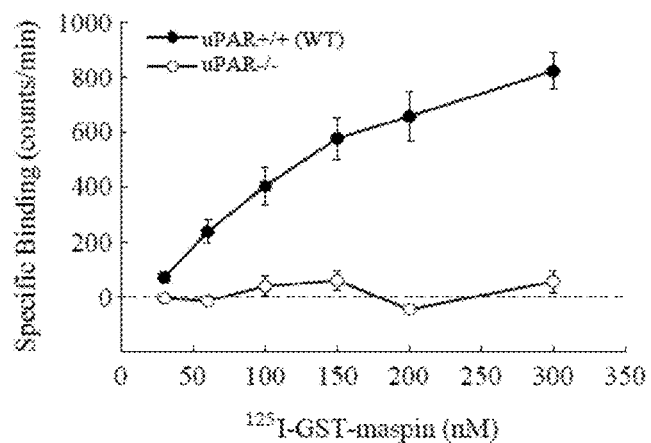
FIG. 3 shows graphs demonstrating that uPAR and uPA/uPAR complex are required for maspin localization to MEF cell surface. (A) Wildtype (WT, black circles) and uPAR−/− (white circles) MEFs were incubated with $^{125}$I-GST-maspin in DMEM containing 5% BSA or at 4° C. for 90 min. Cell surface binding was determined by measuring gamma radiation. (B) Pretreatment of $^{125}$I-GST-maspin with two different maspin antibodies shows that the RCL region is necessary for maspin binding to WT MEF cell surface. The ABS4A antibody (black bars) blocks the RCL region while the S-20 antibody (white bars, Santa Cruz Biotechnology) blocks the N-terminal region. (C) Inhibition of maspin binding to WT MEF cell surface by the antimouse uPAR antibody (R&D), which blocks uPA binding to uPAR. WT MEF cells were treated with the uPAR antibody either without uPA stripping or with uPA stripping and addition of exogenous uPA. Results are reported as GST-maspin binding as a percentage of control (IgG) antibody treatment.
Figure 3:
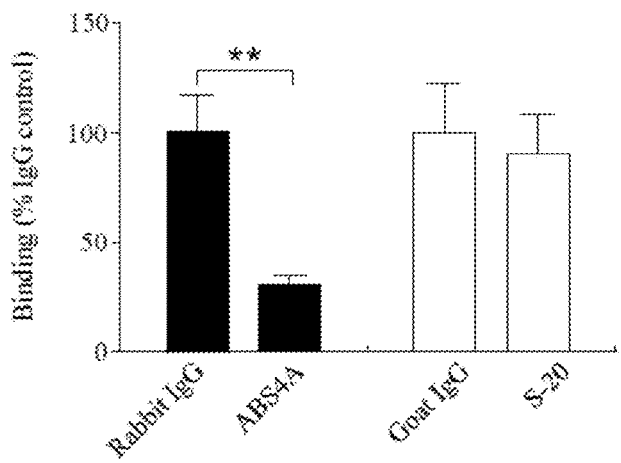
Figure 3:
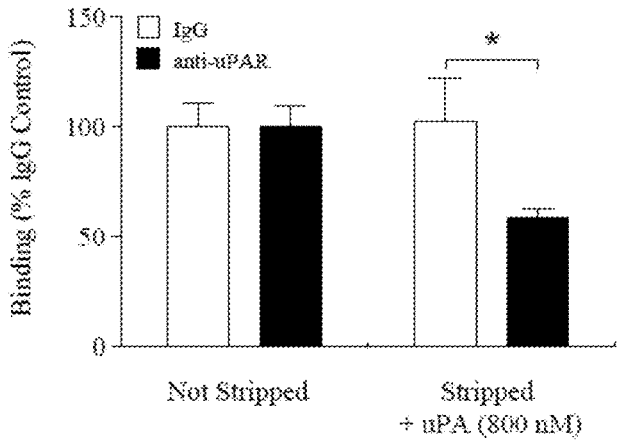

Recent accumulating evidence suggests an important role of the uPA/uPAR complex in regulating cell adhesion (Smith & Marshall, C. J. (2010) *Nat Rev Mol Cell Biol* 11, 23-36; Dass et al. (2008) *Cancer Treat Rev* 34, 122-136; herein incorporated by reference in their entireties). Maspin is localized with the uPA/uPAR complex at the cell surface (Yin et al. (2006) *Cancer Res* 66, 4173-4181; incorporated herein by reference in its entirety); it was investigated whether uPAR is involved in maspin binding to the cell surface. Using WT and uPAR−/− MEFs, it was found that WT MEFs displayed specific 125I-GST-maspin binding while uPAR−/− MEFs were absent of any specific 125I-GST-maspin binding, using concentrations within the normal physiological range (<500 nM) (SEE FIG. 3A). These results indicate that uPAR expression is necessary for maspin to bind or localize to the cell surface.

The binding of $^{125}$I-GST-maspin to WT MEF cells that were incubated with either control (IgG), RCL (ABS4A) or N-terminal (S-20) blocking antibodies was examined Only the RCL (and/or surrounding area) and not the N-terminus of maspin was found to be necessary for maspin binding to the surface of WT MEFs (SEE FIG. 3B).

To determine if the uPA/uPAR complex is required for $^{125}$I-GST-maspin binding to MEF cell surface, an antibody that disrupts uPA binding to uPAR was used. In the first set of experiments, treatment with this antibody did not change the binding of $^{125}$I-GST-maspin to WT MEF cells (SEE FIG. 3C, first set). However, $^{125}$I-GSTmaspin binding to WT MEF cell surface is reduced when cells were stripped of uPA and incubated with the uPAR blocking antibody prior to re-introducing exogenous uPA and 125IGST-maspin (SEE FIG. 3C). These results demonstrated that cell surface localization of maspin requires not only uPAR but the uPA/uPAR complex.

Example 5

Removal of Pericellular uPA Mitigates Maspin-Mediated Cell Adhesion

Maspin binds to both uPA and pro-uPA causing reduced cell attachment by strengthening mature focal adhesion contacts (Yin et al. (2006) *Cancer Res* 66, 4173-4181; incorporated herein by reference in its entirety). Experiments conducted during development of embodiments of the present invention have demonstrated that the amino acid residues from 190-202 and 260-275 in maspin mediate its effect on cell adhesion and these regions are proximal to the RCL (SEE FIG. 2). To whether the association of maspin and uPA may mediate cell adhesion, endogenous uPA was acid-stripped prior to the addition of GST-maspin and evaluated the effect on MCF10A cell adhesion. Stripping uPA substantially blocks maspin-induced MCF10A cell adhesion (SEE FIG. 4A). In order to verify that this ablation of maspin-induced adhesion was a direct effect of uPA removal, uPA-stripped MCF10A cells were resupplied with exogenous uPA (800 nM). Addition of exogenous uPA rescues the maspin-mediated adhesion of uPA-stripped MCF10A cells (154.06% of GST control, SEE FIG. 4A). These experiments demonstrate that uPA is needed for maspin-mediated adhesion.

Example 6

The uPA/uPAR Complex is Necessary for Maspin-Mediated Cell Adhesion

Figure 4:
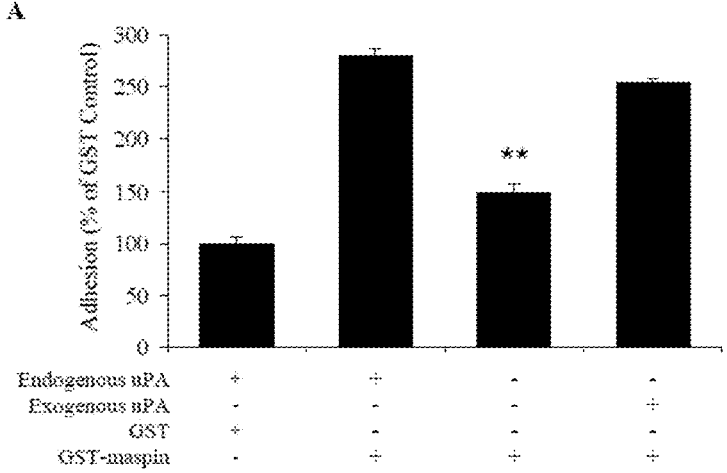
FIG. 4 shows graphs demonstrating that the uPA and uPA/uPAR complex are necessary for maspin-mediated cell adhesion. (A) Stripping endogenous uPA from receptor on cell surface decreases maspin guided cell adhesion to the self-deposited matrix. The GST-maspin-mediated increase in MCF10A cell adhesion was rescued by treatment with exogenous uPA (800 nM). Endogenous uPA was first stripped from MCF10A cell surface, then cells were pretreated with anti-uPAR or rabbit IgG (as a control) at the indicated concentrations for 10 min. Exogenous uPA (800 nM) plus GST-maspin or GST (as a control) were added for another 20 min. MCF10A cells ($2.0\times10^4$) were plated on endogenous matrix and cell adhesion was quantified. (C) MCF10A cells ($2.0\times10^4$) were pretreated with anti-uPAR or rabbit IgG (as a control) at the indicated concentrations for 10 min. GST-maspin or GST (as a control) were added for another 20 min were plated on endogenous matrix and cell adhesion was quantified.
Figure 4:
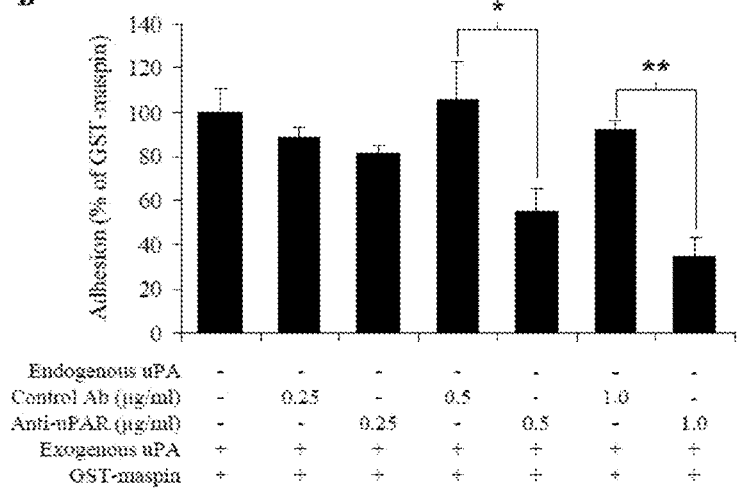
Figure 4:
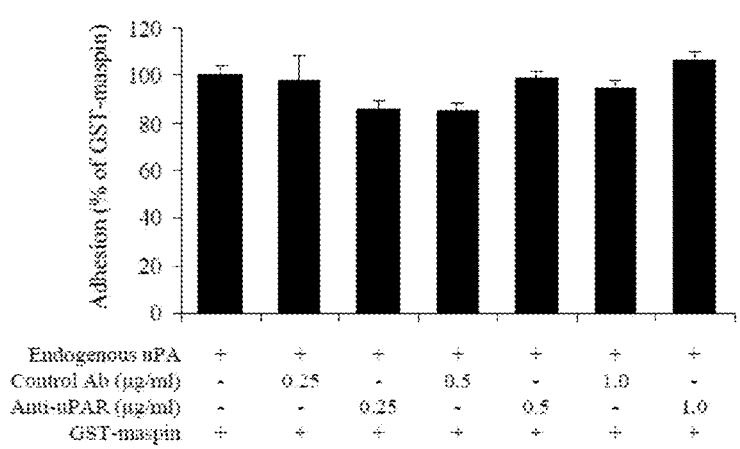

These combined studies revealed that uPAR or uPA removal from the surface of MCF10A cells ablates maspin localization to the cell surface (SEE FIG. 3) and its ability to enhance cell adhesion (SEE FIG. 4A). Experiments were conducted during development of embodiments of the present invention to determine whether uPA and uPAR function independently or if the localization and adhesion functions of maspin require the uPA/uPAR complex. uPAR blocking antibody (antiuPAR, blocks free uPA from binding to uPAR) was used to elucidate the role(s) of the uPA/uPAR complex in maspin-mediated adhesion. Endogenous uPA was stripped from the cell surface and then the cells were incubated with control rabbit IgG or anti-uPAR for 10 min, and finally after the addition of exogenous uPA (800 nM) and GST-maspin (500 nM) the cells were allowed to adhere. At a lower concentration of the anti-uPAR (0.25 mg/ml), there was a slight decrease in cell adhesion, albeit not significant. However, at higher concentration of anti-uPAR (0.5 and 1.0 mg/ml), maspin-mediated MCF10A cell adhesion was significantly inhibited compared to control antibody treatment (SEE FIG. 4B). These findings demonstrate that disrupting uPA binding to uPAR impairs maspin-mediated adhesion. If MCF10A cells are not stripped of uPA, addition of the blocking uPAR antibody has no effect on maspin-mediated cell adhesion (SEE FIG. 4C). The inability of the uPAR blocking antibody to reduce MCF10A cell adhesion implicates the uPA/uPAR complex as effectors of maspin-mediated cell adhesion.

Example 7

Maspin Forms a Complex with uPAR and β1 Integrin

Figure 5:
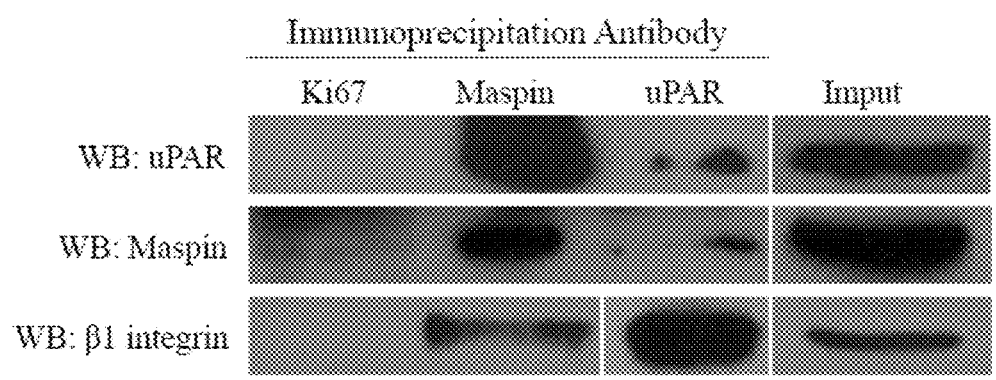
FIG. 5 shows co-immunoprecipitation of maspin with uPAR and β1 integrin. Protein extracts (500 µg) from MCF10A cells overexpressing uPAR were immunoprecipitated with antibodies to uPAR (American Diagnostics), maspin (Pharmingen), and β1 integrin (Chemicon). The Ki67 antibody (Chemicon) was used as a negative control. Eluted immunoprecipitates were separated by SDS-PAGE and analyzed by Western immunoblots.

Experiments were conducted during development of embodiments of the present invention to detect physical association of maspin with both uPAR and β1 integrin to produce a complex that regulates both cell motility and adhesion. The biophysical interaction between maspin, uPAR, and β1 integrin was detected by immunoprecipitating cell lysates from MCF10A cells overexpressing uPAR (SEE FIG. 5). Maspin co-precipitated with both uPAR and β1 integrin. These are the first studies showing the association of all three proteins, the maspin-uPAR-β1 integrin complex.

Example 8

Anti-Angiogenesis Mapsin Peptides

Figure 6:
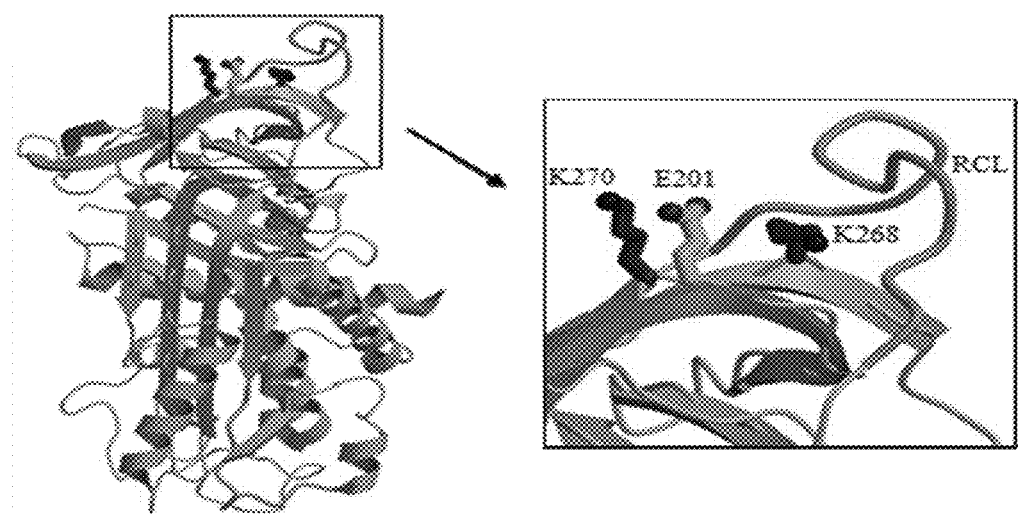
FIG. 6 shows the 3D structure of mapsin. Inset (right panel) indicates that three key amino acids E201, K270, K268 are critical for maspin action.

Experiments were conducted during development of embodiments of the present invention to develop small maspin mimetic peptides for therapeutic treatment. Through maspin deletion and site-specific mutagenesis analysis, the unique region/sites within maspin protein have been identified that are responsible for its binding to cell surface and the mechanism of maspin-mediated signal transduction (SEE FIG. 6). Based on this information, two competitive peptides were designed that act as the antagonist that blocks wildtype maspin's effect on cell adhesion in the range of 0.10-1.0 uM. These two peptides, containing 15 and 22 amino acids respectively, are located in two different regions in primary protein sequence but are spatially very close to each other in the folded protein. Synthetic peptides were tested that contain the key amino acids in both the parental peptides. Amino acid residues were mutated in certain sites in the middle of the peptides. To make the peptides more stable, small peptides were designed (e.g., smaller than 12 amino acids) and were capped at both ends with protective moieties. Peptides were synthesized in high purity and tested in biological assays.

Figure 7:
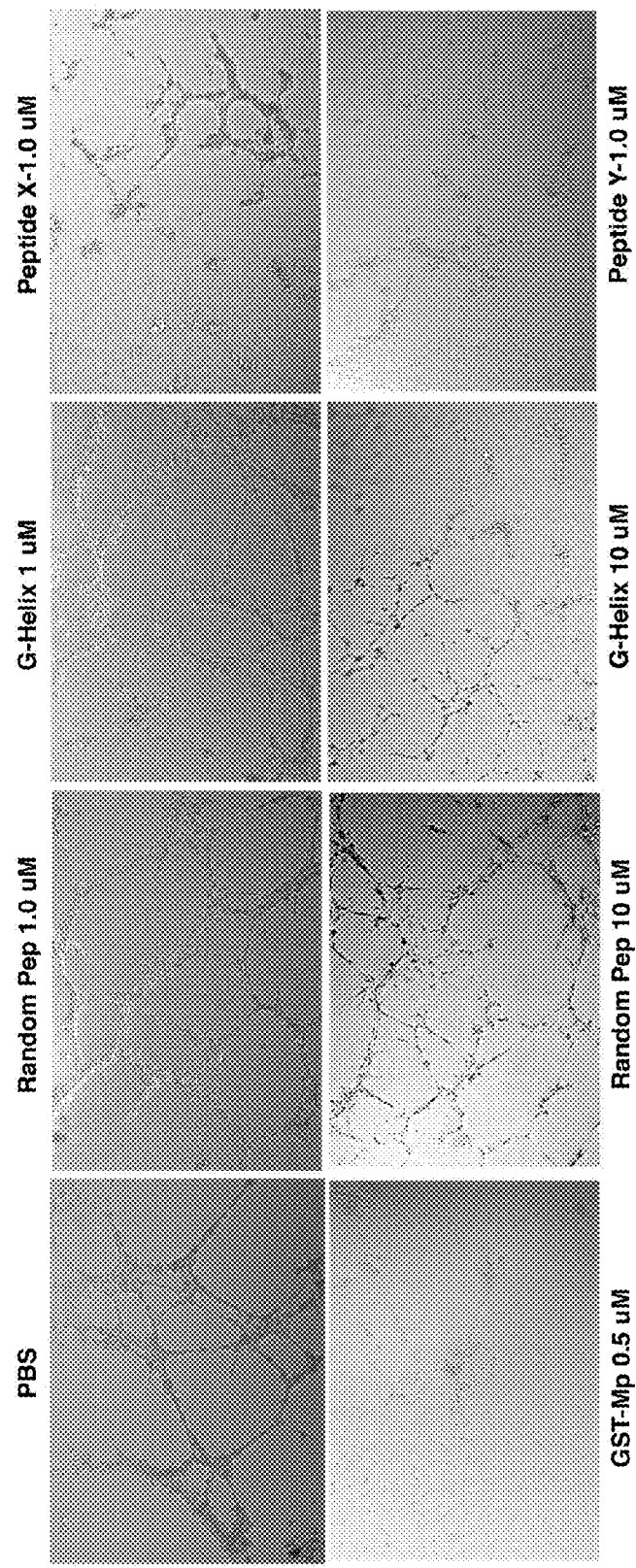
FIG. 7 shows the effect of maspin peptides X and Y on HUVEC tube formation. HUVECs were plated on MatriGel for tube formation assay. Various peptides were tested for the potency on tube angiogenesis. Peptide X and Y were shown to be highly potent compared to the G-Helix peptide or GST-maspin.

HUVEC endothelial cells were used to test the effect of synthetic maspin peptides on HUVEC tube formation assay in cell culture systems. Random peptide was used as a negative control and maspin G-helix peptide as a positive control. G-Helix was previously found to be effective in inhibiting endothelial cell migration, thereby mimicking maspin effect against angiogenesis. G-Helix had a modest effect on HUVEC tube formation at the concentration of 10 uM. At 1.0 uM, G-helix was not effective. However, two of the newly identified peptides: peptide X (STANAKVKLSIP (SEQ ID NO:5)) and peptide Y (TANAEVKLSIPK (SEQ ID NO:6) are highly effective in inhibiting tube formation at a low concentration of 1.0 uM (SEE FIG. 7).

Based on the experiments conducted during development of embodiments of the present invention, it is further contemplated the peptide Z STENAKVKLSIP (Seq ID NO. 7) would also be effective in enhancing cell adhesion and/or inhibits cell motility; inhibiting tube formation; associating with uPAR, β1 integrin, or both; localizing at the cell surface; co-localizing with the uPA/uPAR complex; and/or treating cancer, metastasis, and/or bone formation disorders.

REFERENCES

All publications and patents mentioned in the present application and/or listed below are herein incorporated by reference in their entireties.
1. Zou, Z., Anisowicz, A., Hendrix, M. J., Thor, A., Neveu, M., Sheng, S., Rafidi, K., Seftor, E., and Sager, R. (1994) *Science* 263, 526-529
2. Abraham, S., Zhang, W., Greenberg, N., and Zhang, M. (2003) *J Urol* 169, 1157-1161
3. Seftor, R. E., Seftor, E. A., Sheng, S., Pemberton, P. A., Sager, R., and Hendrix, M. J. (1998) *Cancer Res* 58, 5681-5685
4. Shi, H. Y., Zhang, W., Liang, R., Abraham, S., Kittrell, F. S., Medina, D., and Zhang, M. (2001) *Cancer Res* 61, 6945-6951
5. Shi, H. Y., Liang, R., Templeton, N. S., and Zhang, M. (2002) *Mol Ther* 5, 755-761
6. Zhang, M., Sheng, S., Maass, N., and Sager, R. (1997) *Mol Med* 3, 49-59
7. Zhang, M., Shi, Y., Magit, D., Furth, P. A., and Sager, R. (2000) *Oncogene* 19, 6053-6058
8. Ngamkitidechakul, C., Burke, J. M., O'Brien, W. J., and Twining, S. S. (2001) *Invest Ophthalmol Vis Sci* 42, 3135-3141
9. Cella, N., Contreras, A., Latha, K., Rosen, J. M., and Zhang, M. (2006) *Faseb J* 20, 1510-1512
10. Gao, F., Shi, H. Y., Daughty, C., Cella, N., and Zhang, M. (2004) *Development* 131, 1479-1489
11. Al-Ayyoubi, M., Schwartz, B. S., and Gettins, P. G. (2007) *J Biol Chem* 282, 19502-19509
12. Yin, S., Lockett, J., Meng, Y., Biliran, H., Jr., Blouse, G. E., Li, X., Reddy, N., Zhao, Z., Lin, X., Anagli, J., Cher, M. L., and Sheng, S. (2006) *Cancer Res* 66, 4173-4181
13. Bass, R., Wagstaff, L., Ravenhill, L., and Ellis, V. (2009) *J Biol Chem* 284, 27712-27720
14. Andreasen, P. A., Egelund, R., and Petersen, H. H. (2000) *Cell Mol Life Sci* 57, 25-40
15. Blasi, F., and Carmeliet, P. (2002) *Nat Rev Mol Cell Biol* 3, 932-943
16. Mazar, A. P., Henkin, J., and Goldfarb, R. H. (1999) *Angiogenesis* 3, 15-32
17. Ellis, V., Behrendt, N., and Dano, K. (1991) *J Biol Chem* 266, 12752-12758

18. Jo, M., Thomas, K. S., Wu, L., and Gonias, S. L. (2003) *J Biol Chem* 278, 46692-46698
19. McGowen, R., Biliran, H., Jr., Sager, R., and Sheng, S. (2000) *Cancer Res* 60, 4771-4778
20. Biliran, H., Jr., and Sheng, S. (2001) *Cancer Res* 61, 8676-8682
21. Bass, R., Fernandez, A. M., and Ellis, V. (2002) *J Biol Chem* 277, 46845-46848
22. Odero-Marah, V. A., Khalkhali-Ellis, Z., Chunthapong, J., Amir, S., Seftor, R. E., Seftor, E. A., and Hendrix, M. J. (2003) *Cancer Biol Ther* 2, 398-403
23. Ravenhill, L., Wagstaff, L., Edwards, D. R., Ellis, V., and Bass, R. (2010) *J Biol Chem* 285, 36285-36292
24. Smith, H. W., and Marshall, C. J. (2010) *Nat Rev Mol Cell Biol* 11, 23-36
25. Tarui, T., Andronicos, N., Czekay, R. P., Mazar, A. P., Bdeir, K., Parry, G. C., Kuo, A., Loskutoff, D. J., Cines, D. B., and Takada, Y. (2003) *J Biol Chem* 278, 29863-29872
26. Tarui, T., Mazar, A. P., Cines, D. B., and Takada, Y. (2001) *J Biol Chem* 276, 3983-3990
27. Ma, Z., Thomas, K. S., Webb, D. J., Moravec, R., Salicioni, A. M., Mars, W. M., and Gonias, S. L. (2002) *J Cell Biol* 159, 1061-1070
28. Zhang, M., Volpert, O., Shi, Y. H., and Bouck, N. (2000) *Nat Med* 6, 196-199
29. Langhofer, M., Hopkinson, S. B., and Jones, J. C. (1993) *J Cell Sci* 105 (Pt 3), 753-764
30. Stoppelli, M. P., Tacchetti, C., Cubellis, M. V., Corti, A., Hearing, V. J., Cassani, G., Appella, E., and Blasi, F. (1986) *Cell* 45, 675-684
31. Conlon, M. (2002) *Preparation of 125I-Labeled Peptides and Proteins with High Specific Activity using IODO-GEN*, 2nd Edition Ed. The Protein Protocols Handbook (Walker, J. M., Ed.), Humana Press Inc, Totowa, N.J.
32. Pemberton, P. A., Tipton, A. R., Pavloff, N., Smith, J., Erickson, J. R., Mouchabeck, Z. M., and Kiefer, M. C. (1997) *J Histochem Cytochem* 45, 1697-1706
33. Khalkhali-Ellis, Z., and Hendrix, M. J. (2007) *Cancer Res* 67, 3535-3539
34. Teoh, S. S., Whisstock, J. C., and Bird, P. I. (2010) *J Biol Chem* 285, 10862-10869
35. Goldfinger, L. E., Stack, M. S., and Jones, J. C. (1998) *J Cell Biol* 141, 255-265
36. Goldfinger, L. E., Hopkinson, S. B., deHart, G. W., Collawn, S., Couchman, J. R., and Jones, J. C. (1999) *J Cell Sci* 112 (Pt 16), 2615-2629
37. Dass, K., Ahmad, A., Azmi, A. S., Sarkar, S. H., and Sarkar, F. H. (2008) *Cancer Treat Rev* 34, 122-136
38. Wei, Y., Lukashev, M., Simon, D. I., Bodary, S. C., Rosenberg, S., Doyle, M. V., and Chapman, H. A. (1996) *Science* 273, 1551-1555
39. Wei, Y., Czekay, R. P., Robillard, L., Kugler, M. C., Zhang, F., Kim, K. K., Xiong, J. P., Humphries, M. J., and Chapman, H. A. (2005) *J Cell Biol* 168, 501-511
40. Sheng, S., Carey, J., Seftor, E. A., Dias, L., Hendrix, M. J., and Sager, R. (1996) *Proc Natl Acad Sci USA* 93, 11669-11674
41. Law, R. H., Irving, J. A., Buckle, A. M., Ruzyla, K., Buzza, M., Bashtannyk-Puhalovich, T. A., Beddoe, T. C., Nguyen, K., Worrall, D. M., Bottomley, S. P., Bird, P. I., Rossjohn, J., and Whisstock, J. C. (2005) *J Biol Chem* 280, 22356-22364
42. Al-Ayyoubi, M., Gettins, P. G., and Volz, K. (2004) *J Biol Chem* 279, 55540-55544
43. Sidenius, N., Sier, C. F., and Blasi, F. (2000) *FEBS Lett* 475, 52-56
44. Wilhelm, O. G., Wilhelm, S., Escott, G. M., Lutz, V., Magdolen, V., Schmitt, M., Rifkin, D. B., Wilson, E. L., Graeff, H., and Brunner, G. (1999) *J Cell Physiol* 180, 225-235
45. Cortese, K., Sahores, M., Madsen, C. D., Tacchetti, C., and Blasi, F. (2008) *PLoS One* 3, e3730
46. Czekay, R. P., Kuemmel, T. A., Orlando, R. A., and Farquhar, M. G. (2001) *Mol Biol Cell* 12, 1467-1479
47. Degryse, B., Orlando, S., Resnati, M., Rabbani, S. A., and Blasi, F. (2001) *Oncogene* 20, 2032-2043
48. Nguyen, D. H., Catling, A. D., Webb, D. J., Sankovic, M., Walker, L. A., Somlyo, A. V., Weber, M. J., and Gonias, S. L. (1999) *J Cell Biol* 146, 149-164
49. Madsen, C. D., Ferraris, G. M., Andolfo, A., Cunningham, O., and Sidenius, N. (2007) *J Cell Biol* 177, 927-939
50. Qin, L., and Zhang, M. (2010) *J Biol Chem* 285, 32360-32369
51. Chapman, H. A., Wei, Y., Simon, D. I., and Waltz, D. A. (1999) *Thromb Haemost* 82, 291-297
52. Wei, Y., Yang, X., Liu, Q., Wilkins, J. A., and Chapman, H. A. (1999) *J Cell Biol* 144, 1285-1294
53. Yebra, M., Goretzki, L., Pfeifer, M., and Mueller, B. M. (1999) *Exp Cell Res* 250, 231-240
54. Plopper, G. E., Domanico, S. Z., Cirulli, V., Kiosses, W. B., and Quaranta, V. (1998) *Breast Cancer Res Treat* 51, 57-69
55. Carter, W. G., Ryan, M. C., and Gahr, P. J. (1991) *Cell* 65, 599-610
56. Maass, N., Hojo, T., Zhang, M., Sager, R., Jonat, W., and Nagasaki, K. (2000) *Acta Oncol* 39, 931-934
57. Zhang, M., Magit, D., Botteri, F., Shi, H. Y., He, K., Li, M., Furth, P., and Sager, R. (1999) *Dev Biol* 215, 278-287

What is claimed is:

1. A method of enhancing cell adhesion comprising administering to a cell, tissue, or subject a composition comprising a therapeutically effective amount of a peptide or polypeptide that comprises a portion with at least 90% sequence identity with one or more of SEQ ID NO:1, SEQ ID NO:5, SEQ ID NO:6, and SEQ ID NO:7, wherein the peptide or polypeptide is not full-length mapsin.

2. The method of claim 1, wherein enhancing cell adhesion results in reduced cell motility.

3. The method of claim 1, wherein said cells, tissue, or subject comprises cancer cells, cells at risk of becoming cancerous, or cells at risk of metastasis.

4. The method of claim 1, wherein said peptide or polypeptide physically associates with urokinase receptor (μPAR), β1 integrin, or both upon administering to said cell, tissue, or subject.

5. The method of claim 1, wherein said peptide or polypeptide localizes at the cell surface upon administration to said cells, tissue, or a subject.

6. The method of claim 1, wherein said peptide or polypeptide co-localizes with the uPA/uPAR complex.

7. The method of claim 1, wherein the peptide or polypeptide comprises a portion with 100% sequence identity with one of SEQ ID NO:1, SEQ ID NO:5, SEQ ID NO:6, and SEQ ID NO:7.

8. A method of treating cancer or metastasis comprising administering to a cell, tissue, or subject a composition comprising a therapeutically effective amount of a peptide or polypeptide that comprises a portion with at least 90% sequence identity with one or more of SEQ ID NO:1, SEQ ID NO:5, SEQ ID NO:6, and SEQ ID NO:7, wherein administering said peptide or polypeptide enhances cell adhesion and/or inhibits cell motility, wherein the peptide or polypeptide is not full-length mapsin.

9. The method of claim 8, wherein the peptide or polypeptide comprises a portion with 100% sequence identity with one of SEQ ID NO:1, SEQ ID NO:5, SEQ ID NO:6, and SEQ ID NO:7.

10. A method of treating a bone formation disorder, comprising administering to a cell, tissue, or subject a therapeutically effective amount of a peptide or polypeptide that comprises a portion with at least 90% sequence identity with one or more of SEQ ID NO: 1, SEQ ID NO: 5, SEQ ID NO: 6, and SEQ ID NO: 7, wherein the peptide or polypeptide is not full-length maspin, and wherein administering said peptide or polypeptide treats said bone formation disorder.

11. The method of claim 10, wherein the peptide or polypeptide comprises a portion with 100% sequence identity with one of SEQ ID NO: 1, SEQ ID NO: 5, SEQ ID NO:D 6, and SEQ ID NO: 7.

* * * * *